US012171826B2

(12) United States Patent
Moore et al.

(10) Patent No.: US 12,171,826 B2
(45) Date of Patent: Dec. 24, 2024

(54) HCoV IMMUNOGENIC BOOSTER COMPOSITION FOR IMPROVING IMMUNITYAGAINST SARS-COV-2 INFECTION

(71) Applicants: Timothy S. Moore, Newtown, CT (US); Cullen Thomas Moore, Newtown, CT (US)

(72) Inventors: Timothy S. Moore, Newtown, CT (US); Cullen Thomas Moore, Newtown, CT (US)

(*) Notice: Subject to any disclaimer, the term of this patent is extended or adjusted under 35 U.S.C. 154(b) by 257 days.

(21) Appl. No.: 17/869,306

(22) Filed: Jul. 20, 2022

(65) Prior Publication Data

US 2022/0347290 A1 Nov. 3, 2022

Related U.S. Application Data

(60) Continuation of application No. 17/329,104, filed on May 24, 2021, now abandoned, which is a division of application No. 16/989,796, filed on Aug. 10, 2020, now abandoned.

(51) Int. Cl.

| | |
|---|---|
| *A61K 39/215* | (2006.01) |
| *A61K 33/34* | (2006.01) |
| *A61P 31/14* | (2006.01) |
| *C12N 15/86* | (2006.01) |
| *A61K 39/00* | (2006.01) |

(52) U.S. Cl.

CPC ............ *A61K 39/215* (2013.01); *A61K 33/34* (2013.01); *A61P 31/14* (2018.01); *C12N 15/86* (2013.01); *A61K 2039/5158* (2013.01)

(58) Field of Classification Search

None

See application file for complete search history.

(56) References Cited

U.S. PATENT DOCUMENTS

2022/0040291 A1* 2/2022 Moore .................. A61K 39/12

* cited by examiner

*Primary Examiner* — Stacy B Chen

(57) ABSTRACT

Embodiments include a method of using inactivated human cold coronaviruses (HCoVs) particularly HCoV-299E, HCoV-OC43, HCoV-NL63 and HCoV-HKU1 as a booster, for the immunization against SARS-CoV-2 infections.

4 Claims, No Drawings

HCoV IMMUNOGENIC BOOSTER COMPOSITION FOR IMPROVING IMMUNITY AGAINST SARS-COV-2 INFECTION

CROSS REFERENCE TO RELATED APPLICATIONS

The present application claims priority as a continuation of U.S. patent application Ser. No. 17/329,104, filed May 24, 2021, which is a divisional of U.S. patent application Ser. No. 16/940,313 filed Jul. 27, 2020.

TECHNICAL FIELD

The present invention in an embodiment relates to a method of using inactivated human cold coronaviruses (HCoVs) vaccine, alone or as a booster, for the immunization against SARS-COV-2 infections. Preferred HCoVs are selected from at least one of HCoV-229E, HCoV-OC43, HCoV-NL63 and HCoV-HKU1, and preferably selected from a plurality of such group, and most preferably 3 or all four. In a preferred embodiment the vaccine comprises HCoV virus envelope subunits. In a particularly preferred embodiment the vaccine comprises HCoV virus envelope protein in a virus-like sphere (VLS). One method for inactivation of HCoVs, comprises the steps of exposure to copper atoms followed by hydrogen peroxide treatment. Also provided is a vaccine for immunization against SARS-CoV-2 infection comprising at least one unique protein epitope, or genetic instructions to make such one unique protein epitope, from a plurality of the group of HCOV-229E, HCoV-OC43, HCoV-NL63 and HCoV-HKU1, such unique protein epitope being unique to all other HCoVs in such group, wherein the unique epitopes have epitope homology with SARS-CoV-2 of greater than or equal to 60%. Such HCOV vaccines may be used as a booster, for example, post-immunization with a vaccine designed to produce a specific SARS-COV-2 protein, such as spike protein, to provide for longer lasting effective T-cell memory.

BACKGROUND

A new coronavirus, designated SARS-CoV-2, has ravaged the world since December 2019. This virus first jumped into humans in Wuhan, Hubei Province, China, and then quickly spread across the world. SARS-CoV-2 had never before the infections in China been reported in humans. On Jan. 31, 2020, the Secretary of HHS issued a declaration of public health emergency related to COVID-19. On Mar. 11, 2020 the WHO declared the outbreak of SARS-CoV-2 to be a pandemic. It is estimated that somewhere around 20 percent of infected individuals may develop serious consequences. It is believed that the main cause of transmission is by respiratory droplets, albeit other routes have been hypothesized such as direct human to human contact and fecal to oral contamination. The incubation period of the disease is believed to be 14 days.

Coronaviruses (CoVs) are among the largest known group of viruses in the family Coronaviridae and order Nidovirales. SARS-CoV-2 belong to the Betacoronavirus genus. It has a genome size of approximately 30 kilobases, and is Baltimore class IV positive-sense single-stranded RNA virus. Four structural proteins are encoded in the RNA, spike (S) protein, envelope (E) protein, membrane (M) protein, and nucleocapsid (N) protein. Betacoronaviruses are spherical or pleomorphic in shape having an average diameter of about 125 nm. Coronaviruses are enveloped, that is, have lipid layers.

Recent studies suggest that vaccines can be manufactured to provide protective humoral and cell-mediated immune response against SARS-CoV-2. Many different types of vaccines have been proposed for the immunization against SARS-CoV-2. Vaccine clinical development follows the general pathway as for drugs and other biologics. A sponsor who wishes to begin clinical trails with a vaccine must submit an Investigational New Drug Application (IND) to the FDA. The IND describes the vaccine, its method of manufacture and quality control tests for release. Such also includes information about the vaccine's safety and ability to elicit a protective immune response (immunogenicity) in animal testing, as well as proposed clinical protocol for studies in humans.

Although only a few recombinant technology vaccines have been brought to commercial market to date, of the 164 candidate vaccines reported by the World Health Organization on Jul. 28, 2020 (World Health Organization, Draft Landscape of COVID019 Candidate Vaccines, 31 Jul. 2020), only 11 (7 percent) are employing inactive virus or live attenuated virus, the standard methods of vaccine production (8 using whole or submit inactivated virus, 3 using live attenuated virus) for decades. Of the 25 candidate vaccines in clinical evaluation as of Jul. 28, 2020, five (20 percent) are inactive viruses, suggesting that such technology can still be time competitive in emergencies to vaccines employing recombinant techniques.

SARS-CoV-2 vaccines that employ bioengineering comprise 93 percent of vaccine candidates reported by the World Health Organization on Jul. 28, 2020. While not mutually exclusive, the present technologies are characterized by the WHO in certain set categories.

Replicating or non-replicating viral vector vaccines typically splice in genetic instructions for the S protein of SARS-CoV-2 into a relatively harmless virus (such as Adenovirus Type 5 Vector, or ChAdOx1-S) to cause the cells to mass-produce the protein, with the immune system developing antibodies thereto. Twenty-four of the 164 vaccine candidates as of Jul. 28, 2020 are non-replicating vaccines, while 18 are replicating virus vaccines. To date no non-replicating viral vectors have been licensed for immunity commercially. Three of the 25 candidate vaccines in clinical evaluation as of Jul. 28, 2020 were of the non-replicating viral vector type.

Virus like particle vaccines introduce particles that have enough foreign immunogen to cause the body to produce an immunological response. Virus-like particles are multiprotein structures that mimic the organization and conformation of authentic native viruses but lack the viral genome, and therefore are not infectious. Structurally simple VLPs composed of no more than one or two proteins are normally expressed in bacteria or yeast (with for yeast-based VLPSs vaccines approved for a number of vaccine products). Eukaryotic expression systems, insect and mammalian cells, have been extensively used for both intracellular and secretory production of enveloped VLPs because of their more complex post-translational modification system and that they support most aspects of the virus life cycle. Plant expression systems may also be used. Four commercially available prophylactic VLP vaccines are currently available, GlaxoSmithKline's Engerix (hepatitis B Virus and Cervarix (human papillomavirus), Merck and Co., Inc.s Recombivax HB (hepatitis B Virus) and Gardasil (human papillomavirus). Twelve out of the 164 vaccine candidates identified by the WHO (Jul. 28, 2020) make use of such technology with one of the 25 vaccines in clinical trial as of Jul. 28, 2020 being of this type.

Another technique characterized by the WHO is the protein subunit vaccine, wherein parts of the S protein or Receptor-Binding Domain (RBD) thereof are used to induce an immune response that primes the body to attack the virus. Fifty-five out of the 164 vaccine candidates as of Jul. 28, 2020 are of this type, with 7 out of the 25 in clinical trials as of Jul. 28, 2020 being of this type.

WHO also characterizes numerous vaccines as RNA or DNA based. These vaccines make use of the sequenced SARS-CoV-2 genome (RNA based). Plasmid DNA or RNA, for example, mRNA or viral replicon, are used in the nucleic acid based approaches. DNA plasmid vaccines work by transferring the genetic blueprint to RNA in the cell machinery, which makes spike antigens. When the genetic material is injected into the body it is taken up by cells that being to produce the S protein (most) or other protein, triggering an immune response. RNA is often encased in a lipid coat so it can enter the cell. mRNA vaccines use the host body to produce the viral proteins, thereby bypassing the hassle of producing pure viral proteins, which is thought to sometimes save months or years in standardization and ramping up for mass production. mRNA has the advantage that it cannot become part of a person's chromosomes. The advantage of such vaccines is reducing the task of isolating pure viral proteins. As of Jul. 28, 2020, WHO characterizes 21 vaccines as RNA-based vaccines, and 15 vaccines as DNA based vaccines, with 4 RNA vaccines and 4 DNA vaccines in clinical trials.

One other vaccine that is not specified in the WHO Jul. 28, 2020 list, and does not nicely fit into the classification scheme set forth therein, is a vaccine being developed by Immunor AS, Biovacc-19 (See, Sorensen et al., *Biovacc-19: A Candidate Vaccine of Covid-19 (SARS-CoV-2) Developed from Analysis of its General Method of Action for Infectivity*, Pre-publication print QRB Discovery, DOI 10.017). This vaccine is based on the understanding that antibodies can only recognize 5-6 amino acids. Biovacc-19 is said to be a peptide vaccine designed to develop antibodies to those parts of the SARS-CoV-2 spike protein which are engaged in binding and infecting cells and which are non-human-like in nature. Peptide strings of total length of 30 to 36 amino acids are placed into scaffolds and used to produce an immunological effect.

Inactivated virus vaccines follow the protocol pioneered by Jonas Salk in the early 1950s in the development of the Salk injectable polio vaccine (and later hepatitis A and rabies vaccine), that is they take live viruses and kill them so they cannot replicate. They are differentiated from attenuated vaccines that are created by reducing the virulence of a pathogen, but still keeping it viable (attenuated viruses are typically produced by passage by passage of the virus through a foreign host multiple times until the virus remains active but fairly harmless). Inactive virus vaccines may be known as whole Killed Virus vaccines (WKV) when the entire virus is used in making the vaccine. Albeit, most researchers seeking to rapidly produce a SARS-CoV-2 vaccine rejected what until now has been the gold standard of available vaccines, inactivated and attenuated vaccines, still 1 in 5 having indicated by WHO to have entered clinical trials as of Jul. 28, 2020 are produced by simple inactivation processes. Indeed, out of the six candidate vaccines in Phase 3 as of Jul. 28, 2020, three (fifty percent) are inactivated virus vaccines.

Three major factors have led groups to recombinant technology, first a believed speed in which a consistent vaccine may be made manufactured as compared to standard techniques, second the commercially cheaper expenditure to produce recombinant vaccines, and lastly a belief that inactivated and attenuated viruses include unnecessary antigenic load that contributes little to the protective immune response, and may actually complicate treatment in inducing allergenic and/or reactive responses.

In general the move in vaccine development has been towards biological agents that contain or promote only identified protein epitopes of viruses that are deemed to induce positive, desirable T-cell and B-cell mediated immune responses. Typically the selected peptides are generally 20-20 amino acid sequences. To determine the appropriate epitope candidate multiple predictive algorithms have been developed employing techniques such as nuclear magnetic resonance, X-ray crystallography, mass spectrometry, phage libraries, recombinant cDNA libraries, and mimotopes. Computerized algorithms such as propensity scale, machine-learning algorithm, hybrid algorithm, ABCpred, ANN-BepriPred, HMM, BEDDPRo, SVM and PSSm may be used along with usage of databases containing known T cell-epitopes or peptides. A general discussion of such techniques is set forth in Li, et al. *Peptide Vaccine: Progress and Challenges*, Vaccines 2014: 2:515-536.

In sum, the present vaccine approaches all make use of technologies that either use inactivated or attenuated SARS-CoV-2 virus, or lead to the manufacture of proteins and amino acids that are unique to the SARS-CoV-2 virus.

The neutralization ability of an antibody on a virion is dependent on the strength of interaction between the antibody and antigen and on concentration. When the strength of antibody-antigen interaction is below a certain threshold, a phenomenon known as antibody-dependent enhancement (ADE) may be induced. It has been noted that when primates were vaccinated with a modified vaccinia Ankara virus encoding full-length SARS-CoV glycoprotein and challenged with SARS-COV, the primates suffered from acute lung injury due to ADE. It has been hypothesized that ADE in coronavirus infection may be caused by conformation changes in the spike protein or a high mutation rate of the gene that encodes spike (S) protein. The least conservative amino acids of SARS-CoV-2 appear to be the exposed fragments of the S-protein including the receptor binding domain (RBD)(See, Ricke et al., *Medical Countermeasures Analysis of* 2019-*CoV and vaccine Risks for Antibody-Dependent Enhancement (ADE), SSRN Working paper Series*, doi: 10,21,2139/ssrn.3546070). There is some concern that SARS-CoV-2 vaccines that may initially demonstrate efficacy, may in the future lead to an ADE catastrophe. Testing is underway to reduce such risk.

The present inventors propose herein a radically different approach from the 165 vaccine approaches discussed above, based on the discovery of pre-COVID 19 T-cell cross-reactivity with the SARS-CoV-2 virus and reports of isolated large city (rather than by country or county numbers) SARS-CoV-2 antibody levels and current daily infection and death rates in such cities. Taking note of Edward Jenner's work (Jenner often referred to as the "Father of Immunology") over a century ago using cowpox (indeed the term "vaccine" comes from the word "vacca" meaning cow) as a viral surrogate to prevent smallpox infections (rather than the then known immunization technique of variolation in which material from a small pox pustule was subcutaneously placed into a non-infected person), the present inventors propose a vaccine based on common coronaviruses associated with the common cold as a method of providing prolonged T-cell immunity to SARS-CoV-2 without the fear of ADE, particularly provided as a booster to directed SARS-CoV-2 epitope directed immunizations. ADE is proposed to be reduced by expanding the T-cell immunity pool to more than just isolated spike proteins.

In a recent article by Grifoni et al., *Targets of T Cell Responses to SARS-CoV-2 Coronavirus in Humans with COVID-19 Disease and Unexposed Individuals*, Cell 181: 1489-1501 (Jun. 25, 2020) using blood from 13 samples garnered pre-COVID 19 from 2015-2018 and comparing with 14 convalescing COVID-19 patients, the authors identified regions of the SARS-CoV-2 virus that had cross-reactivity with other common circulating coronaviruses. Concern was raised that such cross-reactive immunity could influence responsiveness to candidate vaccines.

Likewise, in a research paper by Matens et al., *Selective and Cross-Reactive SARS-CoV-2 T-cell Epitopes in Unexposed Humans*, Science 10.1126/Science.abd2871 (2020) the authors identified CD4+ T cells from PBMC samples from unexposed subjects to SARS-CoV-2 that were collected between March 2015 and March 2018 that were cross-reactive to SARS-CoV-2 (82 out of 88). Blood from donors seropositive for common cold coronaviruses (HCoVs) were utilized. Cross reactivity with HCoVs was noted with 142 epitopes derived from SARS-CoV-2 spike, N, nsp8, nsp12, and nsp13. When epitope homology was greater than 67% cross reactivity was noted in 57% of cases (21 out of 37 samples). Strong responses were seen directed to spike, ORF6, ORF3a, N, ORF8 and within Orfa/b, where nsp3, nsp12, nsp4, nsp6, nsp2 and nsp14 were prominently recognized. The authors noted that while it was plausible to hypothesize from the their small sample comparisons that a pre-existing cross-reactivity HCoV CD4+ T cell memory in some donors could be a contributing factor to variations in COVID-19 patient disease outcomes, this is presently highly speculative.

There are many reports of COVID-19 positive test results and total deaths reported daily by the CDC and WHO. The vast majority of these reports are broken down by country and at best state/county within such country. The present inventors have recognized that such totals do not depict clearly what is happening in terms of the spread of SARS-CoV-2 and potential cross immunities that may exist in one or more population. Antibody tests do not tell the whole story. T-cell immunity tests are not widely available. Thus researchers at best have only been able to speculate about possible cross-reactivities between coronaviruses, and the extent that such cross-reactivity may have on a viable immune response.

The inventors have rejected total numbers of cases and deaths in large areas as providing any enlightenment on previously acquired immunities. Instead, they have focused on city data, and reported numbers of antibody seropositive percentages in such areas.

In particular, the inventors have found telling that although NYC has been an epicenter of numerous peaceful and non-peaceful mass actions with large numbers of people taking no heed of purported governmental regulations as to distancing and masking, the number of deaths and reported cases has remained flat from July to August. One of the most recent studies of SARS-COV-2 IgG antibody in NYC, Reifer et al., *SARS-COV-2 IgG Antibody Responses in New York City*, Diagnostic Microbiology and Infectious Disease, 98:115128 (Jul. 1, 2020), indicates that nearly 44% of 28523 patients from the New York City area visiting primary care providers and urgent care facilities in the New York City (the city and the surrounding boroughs of Kings (Brooklyn), Queens, New York (Manhattan), Bronx and Richmond (Staten Island) and surrounding suburbs (Westchester, Rockland, Orange, Nassau and Suffolk counties). In a CDC report updated Jul. 21, 2020, the CDC pegs the overall prevalence of SARS-CoV-2 antibody seroprevalence of NYC between Apr. 26, 2020-May 6, 2020 to be about 23.2 percent, with the lower bound being 19.9% and upper bound 26.3 percent. In Stockholm, as of May 29, 2020 an on going study by the country's Public Health Agency reports nearly 20 percent of Stockholm's population has antibody. In Stockholm, the reports of new COVID-19 deaths have plummeted since the high in April, and so have the number of reported cases. In London, as of May 29, 2020, 17 percent of Londoners were reported to test positive for anti-SARS-COV-2 antibodies by the Office for National Statistics (Burki, Talha Khan, *Testing for COVID-19*, The Lancet: Respiratory Medicine; 8 (7) E63-64 (Jul. 1, 2020). Albeit that London has also been plagued with violent and non-violet protests with protesters not socially distancing or masking appropriately in the summer of 2020, again London has seen a dramatic drop in the number of daily deaths and the number of confirmed COVID-19 cases since July. In Delhi, where nearly one in four residents (25%) of the Indian capital have shown antibodies to SARS-COV-2, positivity ratios are now dramatically reducing as well as deaths. Nearly 50 percent of Mumbai slum cluster residents are now reported to have antibodies to SARS-COV-2, while only 16 percent of the people in the more affluent parts do with highest percentage of deaths occurring outside the slums. Mumbai slum dwellers have a much lower mortality rate of less than 0.05% than compared to city proper dwellers in Mumbai. The increase in reported cases and deaths in Mumbai is highly skewed toward city proper dwellers. The inventors have rejected the hypothesis that the slightly younger population in the slums accounts for such disparity. Rather they reasoned that people in the slums were much more prone to have been exposed to other coronaviruses over their lifetimes, and that immunity from other coronaviruses, such as those causing the common cold, were the basis for the dramatically lower mortality rate.

The present inventors hypothesize that the 20-25 percent antibody findings in respect of large modern disparate cities associated with a decrease in SARS-CoV-2 positivity and dramatically reduced deaths are not happenstance or coincidental. Instead, they reasoned that the long lasting T-cell immunities associated with people affected by multiple coronavirus common colds is adding to the protective effect of B-cell immunity such that the population overall is heading to herd immunity. They note a number of studies that suggest CD4+ T-cells reactive to SARS-CoV-2 epitopes in approximately 50 percent of the population. These studies alone do not provide a basis for determining whether such cross-reactivities are indicative of robust immunity, or alternatively impeding responsiveness to candidate vaccines. The present inventors suggest that the dramatic decreases in cases and deaths noted in large cities as they approach 25% of their population carrying antibodies demonstrate that the CD4+ T-cells reactivities noted by researchers are indeed indicative of robust immunities already native to the population. The fact that the Mumbai slums reached 50% antibody levels, may suggest that such cell mediated immunity may not be perfected in all individuals to ward off SARS-COV-2, and that a population with 25% having antibodies to SARS-CoV-2 may be sufficient to cause dramatic drops in death rates and positivity when done in conjunction with other measures such as social distancing and masking.

They also note that studies on cross reactivity of CD4+ T-cells obtained from persons before the SARS-CoV-2 epidemic, show cross reactivity with samples that were obtained as long ago as 5 years ago. Their review of the data in this light led them to understand that common cold coronaviruses could be used to provide long term cell-mediated immunity to SARS-CoV-2. They thus saw that the T-cell immunity effects noted with respect to common cold viruses could be used as an adjuvant to any primarily B-cell immunity specifically directed SARS-CoV-2 vaccine, or one wherein T-cell immunity is not long lasting. Recent reports indicate that antibodies to SARS-CoV-2 may disappear within as short as three months (See, Liu et al., *Disappearance of antibodies to SARS-CoV-2 in a COVID-19 patient after recovery*, Clinical Microbiology and Infection Jul. 8, 2020 DPO; https//doi.org/10.1016/j.cmi.2020.07.009). While resident B-cell activity after SARS-CoV-2 infection still needs to be determined, such finding suggests that at least some vaccinations that are directed to specific epitopes found on SARS-CoV-2 may not provide long term immunity in the line of years of protection. The present invention proffers an ability to provide long term T-cell mediated immunity in adjunct to any primarily short term B-cell immunity.

The present inventors also hypothesize that ADR is actually more related to a minimization of the profile of T-cells reactive (particular CD4+ T cells) to a virus, rather than just reactivity due to human epitopes found on the virus. Thus, their vaccine provides a booster to any specifically directed SARS-CoV-2 vaccine that is directed to a small subset of viral glycoproteins. The inventors hypothesize little potential reactivity due to common human-like epitopes found on the HCoVs particularly as humans have been exposed to such viruses for a very long period of time, maybe even millennia.

SUMMARY OF THE INVENTION

Accordingly, the invention herein provides in an embodiment a method of using inactivated human cold coronaviruses (HCoVs) vaccine, alone or as a booster, for the immunization against SARS-COV-2 infections. Preferred HCoVs are selected from at least one of HCoV-NL63, HCoV-OC42, HCOV-229E, HCoV-OC43, HCoV-NL63 and HCoV-HKU1, and preferably selected from a plurality of such group, and most preferably 3, more preferably 4 or more, and more preferably 5 or more. In a preferred embodiment the vaccine comprises HCoV virus envelope subunits. In a particularly preferred embodiment the vaccine comprises HCoV virus envelope proteins in a virus-like spheroid (VLS) (which may be approximately ovoid or spherical in shape). Such HCoV vaccine may be used as a booster, for example, post-immunization with a vaccine designed to produce a specific SARS-COV-2 protein, such as spike protein, to provide for longer lasting effective T-cell memory. In an embodiment there is provided a method for inactivation of HCoVs, the method comprising the sequential steps of exposure to copper atoms followed by hydrogen peroxide inactivation. Also provided is a method for separating genomic RNA and nucleoproteins from the lipid protein/glycoprotein shell lipid to allow for formation of VLS by employment of a pH controlled lipophilic to hydrophilic surface.

DESCRIPTION OF SPECIFIC EMBODIMENTS

In one embodiment there is provided a vaccine for improving T-cell immunity, particularly CD4+ T cell immunity, to SARS-COV-2, said vaccine being prepared by (a) providing a plurality of population of cells in cell culture medium; (b) infecting each population of cells by inoculating the population of cells with the at least one of: HCoV-229E, HCoV-OC43, HCoV-NL63 and HCoV-HKU1 and incubating the inoculated population of cells to allow the virus in each cell culture medium to replicate and propagate; (c) collecting the virus from each cell culture medium; (d) purifying each of said virus from each cell culture; (e) inactivating each virus; and (f) preparing a pharmaceutical preparation for inoculation having different antigens from at least two or more of HCoV-229E, HCoV-OC43, HCoV-NL63 and HCoV-KHu1. In such embodiment, the antigens may comprise the whole virus, or part of such virus, from, for example, the virus envelope or a protein associated with the virus. The population of cells may be Vero cells. Inactivation may be at least one of beta propiolactone (BPL), hydrogen peroxide, formalin (formaldehyde) and copper. In one embodiment copper inactivation and hydrogen peroxide inactivation are sequential in order. The vaccine may further comprise an adjuvant one at least of which is selected from alum, Immodulon (IMM-101—containing a heat-killed whole cell *Mobacterium obuense*, a rapidly dividing harmless spaprophyte), algammulin, monphosphoryl lipid A (MPL), resiquimod, muramyl peptide (MPD), N glycolyl dipeptide (GMDP), polyIC, CpG oligonucleotide, aluminum salts, water in oil emulsion and oil in water emulsion.

Deactivation is preferably by exposing the HCoV at one time to copper ions (particularly cupric) and at a distinct time hydrogen peroxide (sequential deactivation). Copper has a free electron in its outer orbital shell of electrons that allows it to easily take part in oxidation-reduction reactions. The copper pokes holes in the Coronavirus lipid coating which allows lower concentrations of other inactivating agents such as beta-propiolactone, formalin or $H_2O_2$ to be used to inactivate the virus. The present inventors have recognized concomitant use is sub-optimal. Whole killed virus, or protein/glycoprotein submits of the viruses may be used in the making of the vaccine.

In another embodiment there is a combination vaccine for immunization against SARS-COV-2 infection comprising at least one unique epitope from each of a plurality in the group of HCoV-NL63, HCoV-OC42, HCOV-229E, HCoV-OC43, HCoV-NL63 and HCoV-HKU1, or the subgroup HCoV-229E, HCoV-OC43, HCoV-NL63 and HCoV-HKU1, of such unique epitope being unique to all other HCoVs in such group, or genetic instructions to make such one unique epitope from each of viruses in the group, wherein the unique epitopes have epitope homology with SARS-COV-2 of greater than or equal to 60%, more preferably greater than 70%, yet more preferably greater than 80%, and yet more preferably greater than 90%, or even more preferably greater than 95%. In a preferred embodiment at least two unique epitopes from each virus of one, two, three, or four in the group is combined, and in a more preferred embodiment at least three unique epitopes from each virus of one, two, three, or four in the group is combined. The unique epitope in each case may be from the RNA virus envelope. The unique epitopes may be limited to cross-reactivity with epitopes of SARS-COV-2 in the SARS-COV-2 spike, N, nsp8, nsp12 and nsp13. The unique epitopes are preferably limited to epitopes found associated with the native HCoV-229E, HCoV-OC43, HCoV-NL63 and HCoV-HKU1 lipid bilayer. The unique epitopes may be naturally-derived, synthetically manufactured, or recombinantly produced. Such unique HCOV epitope vaccine may be used with any of the vaccines noted in the WHO World Health Organization, Draft Landscape of COVID-19 Candidate Vaccines, 31 Jul. 2020, and similar technology based vaccines. In a preferred embodiment, such unique HCOV epitope vaccine is used as a booster such COVID-19 Candidate Vaccines set forth by the WHO 31 Jul. 2020 to provide prolonged cell mediated immunity, particularly through CD4$^+$ T-cells.

Also provided in a vaccine for immunization against SARS-COV-2 infection comprising at least one unique protein epitope, or genetic instructions to make such one unique protein epitope, from a plurality of the group of HCoV-229E, HCoV-OC43, HCoV-NL63 and HCoV-HKU1, such unique protein epitope being unique to all other HCoVs in such group, wherein the unique epitopes have epitope homology with SARS-COV-2 of greater than or equal to 60%. The vaccine may comprises at least two unique protein epitopes, or genetic instruction to make such two unique protein epitopes, are selected from a plurality of the group of HCOV-229E, HCoV-OC43, HCoV-NL63 and HCoV-HKU1. The plurality of the group of HCoV-229E, HCoV-OC43, HCoV-NL63 and HCoV-HKU1 may be three HCoVs. The unique protein epitopes have a homology with SARS-COV-2 epitope of at least greater than or equal to 50%, 60%, 67%, 70%, 80% 90%, or 95%. The vaccine may be used as a booster to a SARS-COV-2 specific vaccine. Preferably the unique protein epitopes have homology of at least 60% with at least one of SARS-CoV-2 spike, N, nsp8, nsp12 or nsp13, and yet more preferably the SARS-COV-spike protein.

Also provided is a vaccine for immunization against SARS-COV-2 infection comprising at three or more unique protein epitopes associated with the lipid membrane from at least two of the group of HCoV-229E, HCoV-OC43, HCoV-NL63 and HCoV-HKU1, such protein epitopes being unique to all other HCoVs in such group, wherein the unique epitopes have epitope homology with SARS-COV-2 of greater than or equal to 65%. The unique protein epitopes may be associated with the lipid membrane. The vaccine of said unique protein epitopes for each virus from the group may be in the form of lipid virus like spheroid particles. The lipid virus like spheroid particles are formed by: (a) selecting copper foam with a copper skeleton of pores around 50 um; (b) immersing the copper foam an aqueous solution of 0.03 M AgNO3 at room temperature; (c) treating the immersed silver foam with a mixed ethanol solution containing HS(CH$_2$)$_{11}$CH$_3$ and HS(CH$_2$)$_{10}$COOH to form a treated copper foam; (d) drying the treated copper foam to form the final treated copper foam (FTCF); (e) running enveloped virus from the group through untreated copper foam followed by the treated copper foam in a pH 7-7.4 solution; (f) releasing materials captured by the final treated copper foam by directing solution with a pH of 10.5-11 over said final treated foam; (g) separating out spheroids having a diameter between 90 nm-150 nm.

Coronaviruses are enveloped with a lipid bilayer, and are believed to induce fusion of the viral envelope with the cell membrane to target cells. Viral fusion glycoproteins are the key epitopes to induce the membrane fusion reaction that allows viral entry. U.S. Pat. No. 6,455,050 to Aventis Pasteur Limited teaches techniques for obtaining viral envelope glycoproteins by means of an appropriate detergent (e.g. Triton X-100 or octylglucoside). Nucleopcapsids are taught to be removable by centrifugation, with viral surface glycoproteins being purified from a glycoprotein enriched fraction by affinity chromatography, such as lentil-lectin and concanavlin A covalently coupled to cross-linked Sepharose or cellulosic microporous membranes. Viral surface glycoproteins are taught to be eluted from the column in the presence of an appropriate competing sugar, such as methyl-D-mannopyranoside, in the presence or absence of salt. Highly purified glycoprotein preparations is said to be obtained in accord with such process (as judged by Coomassie blue or silver stained SDS polyacrylamide gels).

Taught herein is another technique for isolating natural glycoproteins of the lipid bilayer of coronaviruses from the nucleocapsid. Such technique provides lipid bound glycoproteins that may be reannealed into virus like spheroids (VLS). Such as system makes use of highly lipophilic surfaces that can by pH made to switch to highly hydrophilic surfaces. Such technique may be used in conjunction with the with a HCoV vaccine or SARS-COV-2 specific vaccine to provide more immunogenicity as seen with VLP (virus like particles). The present inventors propose that ADR is more likely when the antibody pool is more limited to just a few proteins, such as those found on the spike protein of SARS-CoV-2, and that irrespective of contrary thought, a more robust pool of antibodies may actually reduce ADRs. Such technique makes use of a switchable copper foam having silver deposition followed by surface modification with a mixed solution of thiol containing carboxylic groups and methyl groups (HS(CH$_2$)$_{11}$CHs and HS(CH$_2$)$_{10}$COOH) to provide for pH reversibility between a superhydrophobicity surface and a hydrophilicity surface proposed for removing oil from water. See, Liu et al., *A Smart Switchable Bioinspired Copper Foam Responding to Different pH Droplets for Reversible Oil-Water Separation*, J. Mater. Chem. 2017, (5) 2603-2612, as explained in Example 2 below. The VLS can be formed form at least one of the group of HCOV-229E, HCoV-OC43, HCoV-NL63 and HCoV-HKU1, more preferably at least two of the group, yet more preferably three of the group, or even more preferably form all of the viruses in the group. The VLS spheroids may also be formed from SARS-COV-2 itself. The VLS spheroids can be separated by chromatography, with cryo-electron microscopy being used to detect the same which generally should have diameters of 90-150 nm with glycoprotein protrusions/spikes. The VLS spheroids are then manufactured conventionally into vaccines, which, for example, are used to provide immunity to SARS-COV-2 infections.

Example 1: HCoV Vaccine for Prolonging T-Cell Immunity to SARS-CoV-2

HCOV-229E, HCoV-OC43, HCoV-NL63 and HCoV-HKU1 are isolated from lavage samples, each from multiple persons suffering therefrom to cover the phylogenic tree. Different strains of each HCOV of each is plaque purified and passaged once in Vero cells to generate a P1 stock. The P1 stock is adaptively cultured, passed and expanded on Vero cells. Additional passages are performed to generate, for example, P2 to P5 stocks. Growth kinetics are measured to assure efficient replication and to reach a peak titre of about 6 to 7 log 10 median tissue culture infections dose by 3 or 4 days post infection at a multiplicity of infection of, for example, 0.001 to 0.01 and temperatures between 33° and 37° C. Additional passages are performed to obtain the P$_{final}$ stock (such as P10). Multiple P stocks are sequenced to assure genetic integrity that might affect NAb epitopes. Whole genome of each strain and the P$_{final}$ undergo deep sequencing analysis are undertaken to assure sequence homology of more than about 99.95%. P$_{final}$ stock is propagated in a culture of Vero cells (e.g. 50 liters) using the Cell Factory system. Inactivation is brought about by inactivation with at least one of beta propiolactone (BPL), hydrogen peroxide, formalin (formaldehyde) and copper. Purification is by depth filtration and multiple (e.g. two) steps of chromatography to yield highly pure HCOV stock. Ultrafiltration, size exclusion chromatography and sucrose gradient centrifugation may be used in the purification process. B-propionolactone, for example, may be thoroughly mixed with harvested viral solution at a ratio of 1:4.00 at 2° C.-8° C. Western blot analysis is used to show vaccine stock contains viral structural proteins. Two or more, preferably three or more, of the purified and inactivated HCoV-229E, HCoV-OC43, HCOV-NL63 and HCoV-HKU1 are mixed with an adjuvant one at least of which is selected from alum, Immodulon (IMM-101—containing a heat-killed whole cell *Mobacterium obuense*, a rapidly dividing harmless saprophyte), algammulin, monphosphoryl lipid A (MPL), resiquimod, muramyl peptide (MPD), N glycolyl dipeptide (GMDP), polyIC, CpG oligonucleotide, aluminum salts, water in oil emulsion and oil in water emulsion, and pharmaceutical excipients to form an administrable vaccine. Inactivation should be measured checking for immunogenic response before and after immunization in animals. Dose may be selected by looking at different doses and determining Nab levels at, for example, 7, 14 and 21 days in each of multiple dosing groups. Whole killed virus, or protein/glycoprotein submits of the viruses may be used in the making of the vaccine.

Example 2: Cornavirus Envelope with Attached Glycoprotein Separation from RNA and Nucleoproteins Copper foam with a copper skeleton of pores around 50 um is selected. The foam are immersed in an aqueous solution of 0.03 M AgNO3 at room temperature. The silver treated foam is then treated with a mixed ethanol solution containing $HS(CH_2)_{11}CH_3$ and $HS(CH_2)_{10}COOH$ to form the Final Treated Copper Foam (FTCF). The enveloped virus is exposed to first to untreated copper foam followed by the treated copper foam in a pH 7 solution. Untreated copper ions blast hole into the viral coating, while destroying RNA inside of the virus. Passage through the FTCF at pH 7 makes the FTCF highly hydrophobic while at the same time highly lipophilic. The coronavirus flows through the pores of the copper foam. The coronavirus envelope is deposited along the FTCF at pH about 7-about 7.4 with the RNA and nucleoproteins being washed away in the stream. Release of the attracted lipid from the envelope upon change of pH to more basic pHs may form virus like spheres of natural glycoprotein covered lipid membrane (by changing the pH about the FTCF to about 10.5 to no more than about pH 11 which makes the surface much less lipophilic and more hydrophilic). The pH is carefully controlled to avoid irreversible denaturation of the glycoproteins.

The invention claimed is:

1. An immunogenic composition administration method comprising the steps of: (a) selecting a patient that has been administered an RNA or DNA based vaccine designed to produce a specific SARS-COV-2 protein; (b) administering to said patient at a time after administration of said RNA or DNA based vaccine of step (a), an immunologic pharmaceutical preparation of whole killed virus of two or more of the group consisting of: HCoV-229E, HCoV-OC43, HCoV-NL63, and HCoV-HKU1, wherein the specific SARS-CoV-2 protein of step (a) is a spike protein.

2. The method of claim 1, wherein the RNA-based vaccine of step (a) is a m-RNA based vaccine.

3. The method of claim 1, wherein the DNA-based vaccine of step (a) is a plasmid vaccine.

4. The method of claim 1, wherein the DNA-based vaccine of step (a) is a replicon vaccine.

* * * * *